United States Patent [19]

Su

[11] Patent Number: 5,342,781
[45] Date of Patent: Aug. 30, 1994

[54] EXTERNAL-LOOP PERFUSION AIR-LIFT BIOREACTOR

[76] Inventor: Wei-Wen W. Su, 47-673 Alawiki St., Kaneohe, Hi. 96744

[21] Appl. No.: 92,235

[22] Filed: Jul. 15, 1993

[51] Int. Cl.$^5$ .............................................. C12M 1/04
[52] U.S. Cl. .................................. 435/313; 435/286;
435/287; 435/311; 435/314; 435/813; 210/194;
210/220; 210/221.2; 261/77; 261/123
[58] Field of Search ............... 435/286, 287, 299, 313,
435/314, 813, 311; 261/77, 123; 210/194, 220,
221.2

[56] References Cited

U.S. PATENT DOCUMENTS

| | | | |
|---|---|---|---|
| 2,083,348 | 6/1937 | Scholler et al. | 195/142 |
| 2,422,258 | 6/1947 | Prager | 210/220 |
| 2,542,031 | 2/1951 | Humfeld et al. | 195/137 |
| 3,630,848 | 12/1971 | LeFrancois | 435/314 |
| 3,642,577 | 2/1972 | Gorring | 435/313 |
| 3,660,244 | 5/1972 | Che | 195/43 |
| 3,847,748 | 11/1974 | Gibson et al. | 435/313 |
| 3,957,442 | 5/1976 | Yamamoto et al. | 261/77 |
| 4,207,180 | 6/1980 | Chang | 435/314 |
| 4,704,363 | 11/1987 | Ziegler | 435/313 |
| 4,748,123 | 5/1988 | Birch et al. | 435/314 |
| 4,782,024 | 11/1988 | Scott et al. | 435/247 |
| 4,814,278 | 3/1989 | Hamamoto et al. | 435/286 |
| 4,906,577 | 3/1990 | Armstrong et al. | 435/313 |
| 5,073,496 | 12/1991 | Oosterhuis et al. | 435/813 |
| 5,126,269 | 6/1992 | Fike et al. | 435/284 |

FOREIGN PATENT DOCUMENTS 467689 11/1979 U.S.S.R.
448689 6/1936 United Kingdom.

OTHER PUBLICATIONS

"Novel High Density Perfusion System for Suspension Culture Metabolic Studies" Tyo and Thilly, Nov. 1989. AIChE Annual Meeting.

"Animal Cell Cultivaton for Production of Biological Substances with a Novel Perfusion Culture Apparatus" Sato et al. Journal of Tissue Culture Methods, vol. 8, No. 4, 1983.

*Primary Examiner*—James C. Housel
*Assistant Examiner*—Jan M. Ludlow
*Attorney, Agent, or Firm*—W. Patrick Bengtsson

[57] ABSTRACT

An external-loop perfusion bioreactor for cultivating microbial, plant, animal or insect cells to produce valuable metabolites has a riser conduit; a cell culture medium inlet in the riser conduit; an inlet for an oxygen containing gas in the riser conduit; a downcomer conduit, having an upper portion and a lower portion, the upper portion of the downcomer conduit being in the shape of a truncated cone; an upper and lower transfer conduit connecting the riser conduit and the downcomer conduit; a spent medium outlet port defining a liquid level surface in the upper portion of the downcomer conduit; and a baffle means having a fluid impermeable wall for creating a settling zone in the upper portion of the downcomer conduit. A series of conical lamellar settling surfaces can be arranged in the settling zone to enhance particle separation from the aqueous medium.

7 Claims, 4 Drawing Sheets

EXTERNAL-LOOP PERFUSION AIR-LIFT BIOREACTOR

FIELD OF THE INVENTION

The present invention relates to external-loop perfusion air-lift bioreactors, and in particular, to an external-loop perfusion air-lift bioreactor having a particularly advantageous settling zone design in the downcomer portion thereof.

BACKGROUND OF THE INVENTION

A variety of biological reactors including standard fermenters and specialty bioreactors have been used to produce primary and secondary metabolites from mammalian, plant, and insect cells, bacteria, yeasts, and fungi. As the use of recombinant proteins and other metabolites increases, the demand for efficient and cost effective biological reactors is expected to increase.

The importance of developing an efficient culture perfusion system has been repeatedly addressed in the literature. The most critical element in a culture perfusion system is the cell/medium separator. There are two major classes of techniques for the separation of cells from the medium in perfusion bioreactors, namely, by gravitational or centrifugal sedimentation, and by tangential filtration (e.g. axial rotation filtration such as spin filters or cross flow filtration).

Sato et al. (*Journal of Tissue culture Methods.* 8: 167–171, 1983), describe an internal conical cell separator consisting of a tapered conical sedimentation chamber affixed to the headplate of a bioreactor. Spent medium is extracted through the top of the cone and cells settle and slide down the steep walls of the cone to the fermenter.

Kitano et al. (*Journal of Applied Microbiology and Biotechnology,* 24:282–286 1986), describe a modified version of the system developed by Sato et al which uses a conical cell precipitator placed above the bioreactor and connected by tubes to the culture to separate cells from media.

Tyo and Thilly, in their paper presented at the section of *New Developments in Mammalian Cell Reactor Studies,* Annual Meeting, American Institute of Chemical Engineers (AICHE), 1989, describe a system consisting of a series of nested truncated cones with an innermost solid cone. Cells and medium are pumped up through the cones while cells are collected on the lower surface of the cones, thereby resulting in a virtually cell-free fluid.

The above mentioned designs have the settler inserted directly into the turbulent well-mixed region of the bioreactor and therefore the sedimentation process is vulnerable to disturbance by fluid turbulence. In addition, the entrance into the above settlers is small and therefore clogging can occur.

It is an object of the present invention to provide a perfusion air-lift bioreactor for cultivating microbial, plant, animal or insect cells to produce valuable metabolites in which improved cell/medium separation can be achieved. It is another object of the invention to provide such a reactor in which disturbance to particle sedimentation is minimized.

SUMMARY OF THE INVENTION

In order to meet these and other objectives, the present invention relates to an external-loop perfusion bioreactor for cultivating microbial, plant, animal or insect cells to produce valuable metabolites. In this perfusion bioreactor, cells can be efficiently cultured and retained with constant replenishment of the nutrient medium solution.

The external-loop perfusion bioreactor of the present invention generally comprises: (1) a riser conduit; (2) cell culture medium inlet in the riser conduit; (3) an inlet for an oxygen containing gas in the riser conduit; (4) a downcomer conduit, having an upper portion and a lower portion, the upper portion of the downcomer conduit being in the shape of a truncated cone; (5) an upper transfer conduit connecting an upper portion of the riser conduit to the upper portion of the downcomer conduit; (6) a lower transfer conduit connecting a lower portion of the downcomer conduit to a lower portion of the riser conduit; (7) a spent medium outlet port defining a liquid level surface in the upper portion of the downcomer conduit; and (8) baffle means comprising a fluid impermeable wall for creating a settling zone in the upper portion of the downcomer conduit, wherein the fluid impermeable wall comprises a generally T-shaped baffle conduit having a baffle conduit inlet connected to the upper transfer conduit and two baffle conduit outlets, a first one of the baffle outlets extending through the upper portion of the downcomer conduit and above the liquid level surface, and a second one of the baffle outlets extending away from the liquid surface.

Preferably, the bioreactor of the present invention further comprises at least one settling surface in the shape of a truncated cone positioned in the settling zone. More preferably, the bioreactor includes a series of lamella settling surfaces, each of the surfaces being in the shape of a truncated cone, arranged in the settling zone.

Another aspect of the present invention relates to a means for improving the efficiency of particle separation from the aqueous medium. This is accomplished by terminating the conical section of the downcomer at a position along a length of the downcomer conduit and terminating the second baffle outlet at a position upstream from the position at which the conical section terminates. Thus, the downward fluid motion in the downcomer drives the cell particles away from the settling zone, and therefore improves the efficiency of separation.

A further embodiment of the invention includes the use of membrane tubing to aerate the settling zone without disturbing particle sedimentation. Additionally, or separately, the bioreactor may contain a fluid surface aerator for aerating liquid at the liquid level surface.

BRIEF DESCRIPTION OF THE DRAWINGS

The following description will be more fully understood with reference to the accompanying drawings in which.

DETAILED DESCRIPTION OF THE PREFERRED EMBODIMENTS

Figures 1A, 1B:
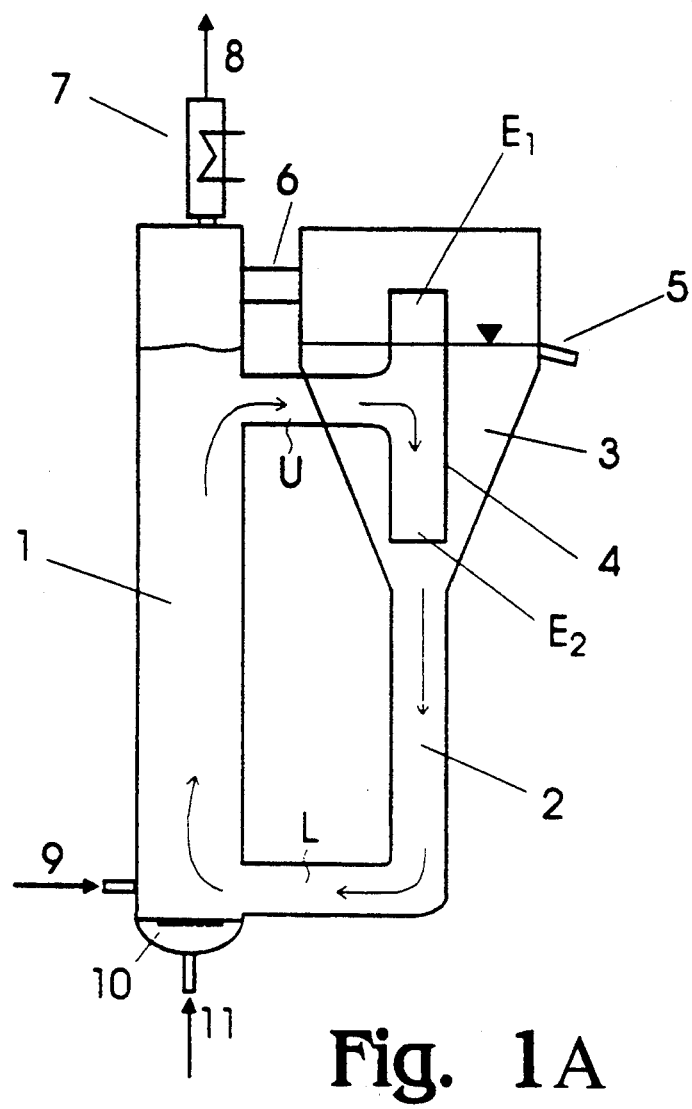
FIGS. 1a and 1b illustrate a vertical sectional view and a top view, respectively, of an external-loop air-lift bioreactor of the present invention.

Referring now to FIG. 1 wherein the external-loop air-lift perfusion bioreactor of the present invention is shown, the bioreactor of the invention first comprises a riser conduit 1 and a downcomer conduit 2. The upper portion of riser conduit 1 is connected to the upper portion of downcomer conduit 2 by a transfer conduit U to form the upper arm of the external loop in the bioreactor. Similarly, the lower portion of riser conduit 1 is connected to the lower portion of downcomer conduit 2 by a transfer conduit L to complete the loop from the lower portion of the bioreactor.

In a preferred embodiment, the main body of the bioreactor is made of glass. Glass is the preferred material because it is compatible with common sterilization techniques such as moist heat sterilization. However, the bioreactor can be made from a variety of materials such as stainless steel. Stainless steel is particularly preferred when the bioreactor is used for large scale perfusion applications.

In FIG. 1 riser conduit 1 further comprises a fresh medium inlet 9. Fresh medium inlet 9 is fixed to the side wall near the bottom of the riser conduit 1. Fresh medium inlet 9 is used to provide constant replenishment of the nutrient medium solution and thus, the nutrient medium can be continuously fine-tuned to achieve high cell density and metabolite productivity.

Riser conduit 1 further comprises an air (or other gas as desired in the reactor, such as oxygen) inlet 11 and a perforated plate 10. Air inlet 11 is fixed to the bottom wall of riser conduit 1. Perforated plate 10 is located inside riser conduit 1, at a position above the internal opening of air inlet 11, but below the connection point of the lower portion of riser conduit 1 and transfer conduit L. Air inlet 11 provides a steady stream of gas which enters the culture medium through perforated plate 10. The sparging of air from the bottom of the riser conduit 1 creates a bulk density difference between the fluids in riser conduit 1 and in downcomer conduit 2, and therefore generates fluid circulation. Fluid circulation further creates a well mixed zone throughout the entire external-loop perfusion bioreactor except in a part of the upper portion of the downcomer conduit 2 defined as the settling zone 3.

Further shown by FIG. 1 is condenser 7 and an air outlet 8. Condenser 7 is fixed on the top of riser conduit 1 through an inner opening whose function is to reduce water evaporation due to air sparging into riser conduit 1.

Downcomer conduit 2 of the preferred embodiment comprises, or may consist of, an upper portion and a lower portion, the upper portion of downcomer conduit 2 being in the shape of a truncated cone. The truncated cone provides a gradually enlarged (enlarging) cross-sectional area towards the top of downcomer conduit 2, which has the function of reducing linear liquid rising velocity in the truncated cone and therefore improves particle separation.

Inside the truncated cone, a settling zone 3 is created by a baffle means. The baffle means of the preferred embodiment of the present invention comprises a fluid impermeable wall 4 for defining settling zone 3 in the upper portion of downcomer conduit 2. Fluid impermeable wall 4 comprises a generally T-shaped baffle conduit having a baffle conduit inlet connected to upper transfer conduit U and two baffle conduit outlets $E_1$ and $E_2$, where outlet $E_1$ extends through the upper portion of the downcomer conduit 2 and above the liquid level surface, and outlet $E_2$ extends away from the liquid surface, in the downward direction along downcomer conduit 2. The T-shaped baffle conduit has the advantage of directing fluid flow and reducing the disturbance to cell sedimentation in the settling zone 3.

The T-shaped baffle conduit allows gas bubbles carried by the circulating liquid from the upper transfer conduit U to be freely vented to the reactor headspace above the liquid level in the downcomer through $E_1$. This arrangement permits fewer gas bubbles to move into settling zone 3 that may cause potential disturbance to particle sedimentation.

Further shown in FIG. 1 is a spent medium overflow 5. The outlet port of spent medium overflow 5 defines a liquid level surface in the upper portion of downcomer conduit 2. The medium overflow device enables the spent medium to be removed without the need of an additional pump and it further reduces the disturbance to cell sedimentation in the settling zone 3.

The perfusion bioreactor of the present invention further comprises a pressure equilibrating conduit 6. Pressure equilibrating conduit 6 is located above the liquid level defined by spent medium overflow 5. It provides a connection between the upper portion of riser conduit 1 and downcomer conduit 2. Pressure equilibrating conduit 6 is incorporated to equilibrate the head space pressure in the downcomer and the riser. The pressure generated inside the bioreactor due to the sparging of air can be released through air outlet 8.

Figure 2:
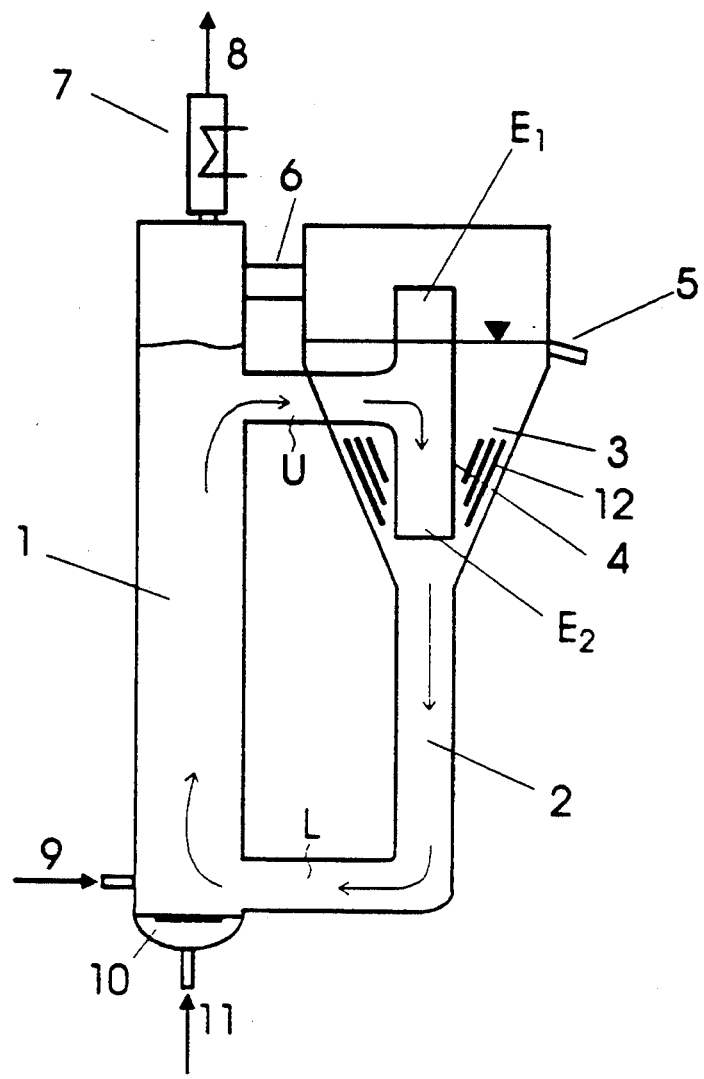
FIG. 2 is a vertical sectional view of an external-loop air-lift bioreactor which incorporates conical lamella settling plates into the settling zone.

Referring now to FIG. 2, the bioreactor of the present invention can also include at least one settling surface in the shape of a truncated cone positioned in settling zone 3. Preferably, the bioreactor includes a series of conical lamella settling plates 12. Each of the settling plates is in the shape of a truncated cone, arranged in settling zone 3. As culture fluid flows upwardly toward spent medium overflow 5 between the surfaces of the parallel cones, particles settle onto the upper surfaces of the cones and slide down into the portion of downcomer conduit 2 where the truncated cone portion of the downcomer meets the cylindrical lower portion. In this manner, clarified virtually cell free spent medium can be withdrawn via overflow 5. Cell sedimentation in the bioreactor is enhanced by way of the parallel inclined walls in the settling zone 3 which results in a large sedimentation surface area and reduced culture fluid superficial upflow velocity due to the enlarged cross section area.

Figure 3:
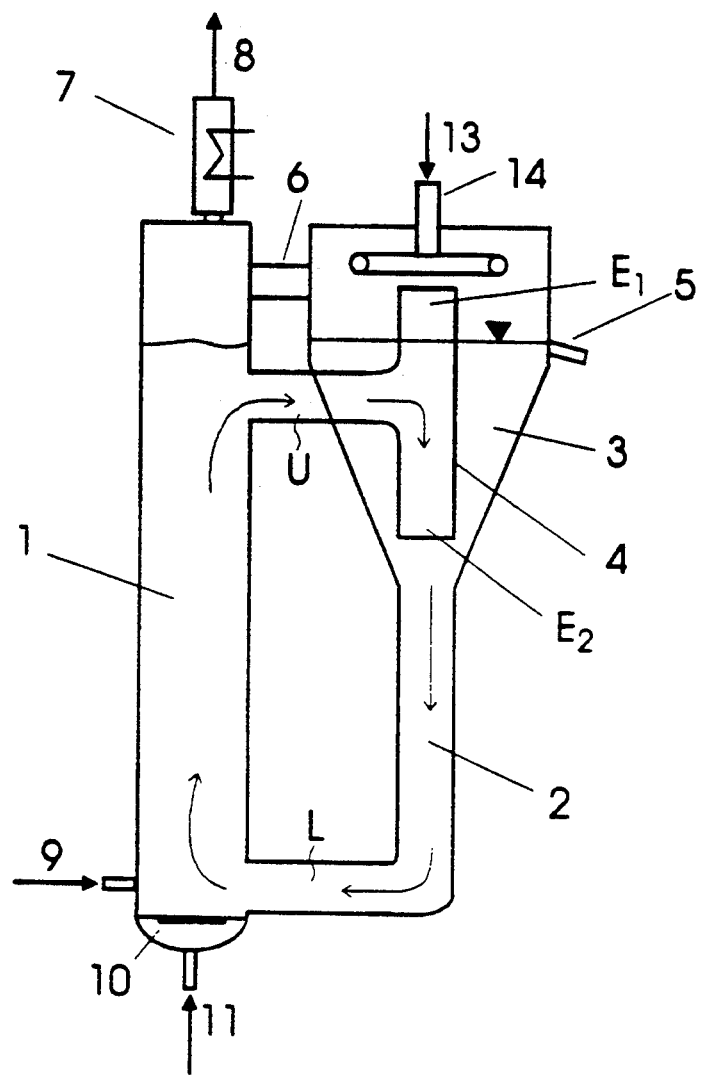
FIG. 3 is a vertical sectional view of an external-loop air-lift bioreactor which incorporates a surface aerator.

Referring now to FIG. 3, the bioreactor of the present invention further comprises a surface aerator 14 and an air inlet 13. Surface aerator 14 is installed above the first T-shaped baffle conduit outlet $E_1$ which extends through the upper portion of the downcomer conduit 2 and above the liquid level surface. Air inlet 13 is connected to the top of surface aerator 14 to provide the input of an oxygen containing gas. Surface aerator 14 provides oxygen to settling zone 3 without disturbing the particle sedimentation. Surface aerator 14 can be in the form of a ring sparger or a gas manifold.

Figure 4:
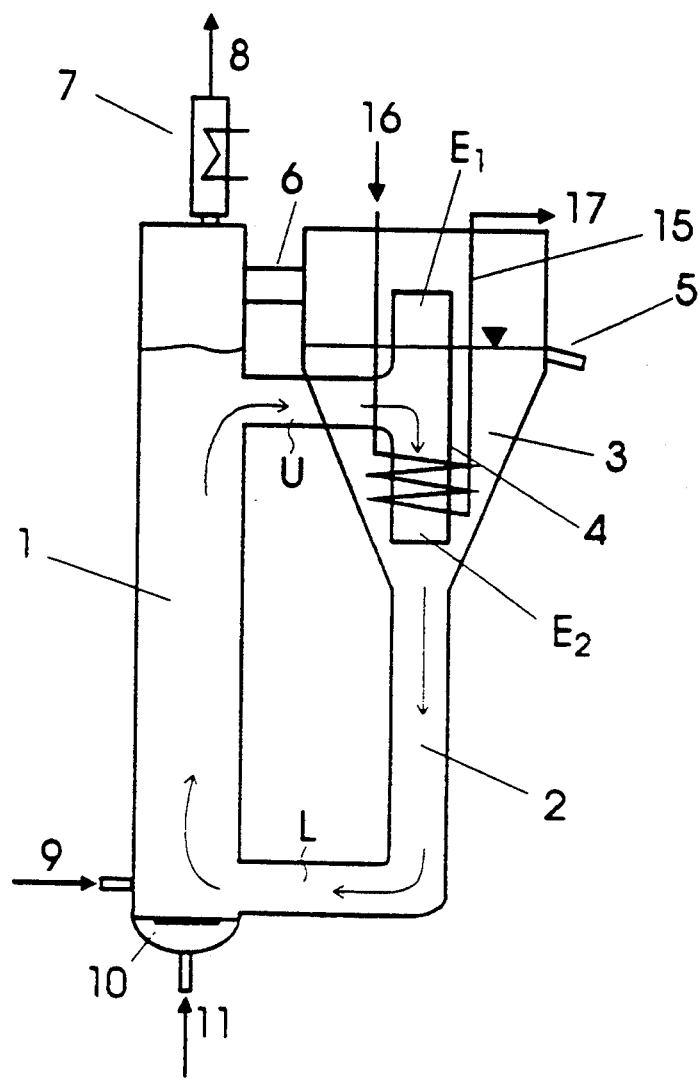
FIG. 4 is a vertical sectional view of an external-loop air-lift bioreactor which incorporates membrane tubing in the settling zone for bubble-free aeration.

Referring now to FIG. 4, the bioreactor of the present invention can also utilize membrane tubing 15. Tubing 15 is an oxygen permeable membrane positioned within settling zone 3. In a preferred embodiment, tubing 15 can be an oxygen permeable silicone membrane or microporous polymer membrane coiled within settling zone 3 to provide bubble-free aeration.

Membrane tubing 15 comprises gas inlet 16 at its first end and a gas outlet 17 at the its second end. Gas inlet 16 is used to guide the input of oxygen from outside sources into membrane tubing 12. The excessive oxygen which does not diffuse out of the tube will remain in membrane tubing 15 and flows out of the bioreactor through air outlet 17.

The foregoing description is intended primarily for purposes of illustration. The perfusion bioreactor of the present invention may be embodied in other forms or carried out in other ways without departing from the spirit or scope of the invention. Modifications and variations still falling within the spirit or the scope of the present invention will be readily apparent to those of skill in the art, and are considered to fall within the scope of the appended claims.

I Claim:

1. An external-loop perfusion bioreactor for cell culture comprising:
   (a) a riser conduit;
   (b) cell culture medium inlet in said riser conduit;
   (c) an inlet for an oxygen-containing gas in said riser conduit;
   (d) a downcomer conduit, having an upper portion and a lower portion, said upper portion of said downcomer conduit being in the shape of a truncated cone;
   (e) an upper transfer conduit connecting an upper portion of said riser conduit to said upper portion of said downcomer conduit;
   (f) a lower transfer conduit connecting said lower portion of said downcomer conduit to a lower portion of said riser conduit;
   (g) a spent medium outlet port defining a liquid level surface in said upper portion of said downcomer conduit; and
   (h) baffle means comprising a fluid impermeable wall defining a settling zone in said upper portion of said downcomer conduit, wherein said fluid impermeable wall comprises a generally T-shaped baffle conduit having a baffle conduit inlet connected to said upper transfer conduit and two baffle conduit outlets, a first one of said baffle outlets extending through said upper portion of said downcomer conduit and above said liquid level surface, and a second one of said baffle outlets extending downward from said liquid surface.

2. A bioreactor as in claim 1 wherein a lower portion of said truncated cone terminates at a position along a length of said downcomer conduit and said second baffle outlet terminates at a position above the position at which said truncated cone terminates.

3. A bioreactor as in claim 1 further comprising a fluid surface aerator positioned in said downcomer conduit for aerating liquid at said liquid level surface.

4. A bioreactor as in claim 1 further comprising oxygen permeable membrane tubing positioned within said settling zone.

5. A bioreactor as in claim 1, further comprising at least one settling surface in the shape of a truncated cone positioned in said settling zone.

6. A bioreactor as in claim 5 including a series of lamellar settling surfaces, each said surface being in the shape of a truncated cone, arranged in said settling zone.

7. A bioreactor for cell culture comprising:
   (a) a riser conduit having a generally cylindrical shape, an upper portion and a lower portion, a cell culture medium inlet, and an oxygen-containing gas inlet in said lower portion, a centerline of said riser conduit between said lower and upper portions of said riser conduit defining a substantially vertical axis;
   (b) a downcomer conduit having an upper portion and a lower portion, a centerline of said downcomer conduit between said upper and lower portions defining a substantially vertical axis, said upper portion of said downcomer conduit having the shape of a truncated cone, and said upper portion of said downcomer conduit including a spent medium outlet, said spent medium outlet defining a liquid level surface;
   (c) an upper transfer conduit connecting said upper portion of said riser conduit and said upper portion of said downcomer conduit, a centerline of said upper transfer conduit defining a substantially horizontal fluid flow path therebetween;
   (d) a lower transfer conduit connecting said lower portion of said downcomer conduit and said lower portion of said riser conduit, and a centerline of said lower transfer conduit defining a substantially horizontal fluid flow path therebetween;
wherein said upper transfer conduit extends into said upper portion of said downcomer and has two outlet conduits, a first one of said outlet conduits extending in a direction generally parallel to said vertical axis, and forming an outlet port above said liquid level surface, a second one of said outlet conduits extending in a direction generally parallel to said vertical axis and in a direction opposite said direction in which said first outlet conduit extends, and said second outlet conduit forming an outlet port in a lower portion of said truncated cone.

* * * * *